(12) United States Patent
Nachman et al.

(10) Patent No.: US 10,357,199 B2
(45) Date of Patent: Jul. 23, 2019

(54) SLEEP AND ENVIRONMENT MONITOR AND RECOMMENDATION ENGINE

(71) Applicant: Intel Corporation, Santa Clara, CA (US)

(72) Inventors: Lama Nachman, San Francisco, CA (US); Rita H. Wouhaybi, Portland, OR (US); Sangita Ravi Sharma, Portland, OR (US); Jonathan J. Huang, Pleasanton, CA (US); Jennifer Anne Healey, San Jose, CA (US); Lenitra M. Durham, Beaverton, OR (US); Chieh-Yih Wan, Beaverton, OR (US); Omar Ulises Florez Choque, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 161 days.

(21) Appl. No.: 15/473,970

(22) Filed: Mar. 30, 2017

(65) Prior Publication Data
US 2018/0279946 A1    Oct. 4, 2018

(51) Int. Cl.
*A61B 5/00* (2006.01)
*A61B 5/08* (2006.01)
(Continued)

(52) U.S. Cl.
CPC ........ *A61B 5/4815* (2013.01); *A61B 5/02055* (2013.01); *A61B 5/7246* (2013.01); *A61B 5/024* (2013.01); *A61B 5/02405* (2013.01); *A61B 5/0476* (2013.01); *A61B 5/0533* (2013.01); *A61B 5/08* (2013.01); *A61B 5/11* (2013.01); *A61B 5/165* (2013.01); *A61B 5/4803* (2013.01); *A61B 5/4812* (2013.01); *A61B 5/6802* (2013.01); *A61B 5/7264* (2013.01); *A61B 5/7282* (2013.01); *A61B 2560/0242* (2013.01); *A61B 2562/0204* (2013.01); *A61B 2562/0219* (2013.01)

(58) Field of Classification Search
CPC ... A61B 5/4812; A61B 5/4815; A61B 5/7275; A61B 5/4806; A61B 5/4809
See application file for complete search history.

(56) References Cited

U.S. PATENT DOCUMENTS

2017/0065792 A1*   3/2017   Bonvallet ............ A61B 5/4806

OTHER PUBLICATIONS

"My Fitness Pal", [Online]. Retrieved from the Internet: <URL: https://www.myfitnesspal.com/>, (Accessed on Sep. 28, 2017), 6 pgs.

(Continued)

*Primary Examiner* — John R Downey
(74) *Attorney, Agent, or Firm* — Schwegman Lundberg & Woessner, P.A.

(57) ABSTRACT

In some embodiments, the disclosed subject matter involves identifying environmental factors and user context that affect sleep quality. Embodiments use information about the static sleep environment, as well as dynamic environmental factors, such as sound, light, movement, correlated with user context, such as physical and emotional state, as well, as recent behavior to classify sleep data. The correlated and classified sleep data may be used to provide change recommendations, where implementing the recommended change is believed to improve the user's sleep quality. Other embodiments are described and claimed.

25 Claims, 4 Drawing Sheets

(51) Int. Cl.
*A61B 5/11* (2006.01)
*A61B 5/16* (2006.01)
*A61B 5/024* (2006.01)
*A61B 5/053* (2006.01)
*A61B 5/0205* (2006.01)
*A61B 5/0476* (2006.01)

(56) References Cited

OTHER PUBLICATIONS

Kay, Matthew, et al., "Lullaby: A Capture & Access System for Understanding the Sleep Environment", UbiComp '12, (Sep. 2012), 10 pgs.

* cited by examiner

SLEEP AND ENVIRONMENT MONITOR AND RECOMMENDATION ENGINE

TECHNICAL FIELD

An embodiment of the present subject matter relates generally to monitoring sleep quality of a user, and more specifically, to monitoring characteristics of sleep quality correlated with environmental factors, and providing automatic recommendations to the user.

BACKGROUND

Various mechanisms exist for monitoring wakefulness and sleep quality. However, people still struggle with getting enough quality sleep. There are over the counter products that measure the movement or stillness of the sleeper to identify restlessness in a sleep pattern. There are sleep studies to measure things such as eye movements, blood oxygen levels in your blood, heart and breathing rates, snoring, and body movements. A sleep study is often conducted in a room that is made to be comfortable, quiet and dark for sleeping.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

In the following description, for purposes of explanation, various details are set forth in order to provide a thorough understanding of some example embodiments. It will be apparent, however, to one skilled in the art that the present subject matter may be practiced without these specific details, or with slight alterations.

Embodiments of the present subject matter are a system and method relating to monitoring a person's sleep quality correlated with environmental factors, or context. One of the biggest failures of existing sleep monitoring methods is that they do not measure environmental factors and correlate them with sleep quality. Sometimes poor sleep quality is caused by stress or anxiety, but many times it is related to environmental issues. People may spend a lot of money on improving the environment in their homes, for instance, buying window blinds or shades to reduce light coming in, investing in double and triple pane windows to reduce outside noise, buying a quieter heating system/appliances, or even remodeling their home to move the sleeping area to another location in the house. Sometimes a person may sleep in a separate bedroom from their significant other due to snoring or excessive sleep movement. But these attempts to improve sleep quality may prove fruitless because the decisions are not data driven. People may have a perception of what might be interrupting their sleep, but the preconceived assumptions may not be accurate.

In at least one embodiment, a data driven approach is used to provide people with recommendations for improving their sleep quality, based on physical, emotional and environmental factors. With appropriate recommendations, investment decisions may be better made by characterizing the impact of different environmental factors on actual sleep interruption and sleep quality. Sometimes, a simple behavioral change may be all that is needed to improve sleep quality. Analysis of the sleep quality correlated with environmental factors allows insight into root causes of poor sleep, and enables users to make better tradeoffs.

Reference in the specification to "one embodiment" or "an embodiment" means that a particular feature, structure or characteristic described in connection with the embodiment is included in at least one embodiment of the present subject matter. Thus, the appearances of the phrase "in one embodiment" or "in an embodiment" appearing in various places throughout the specification are not necessarily all referring to the same embodiment, or to different or mutually exclusive embodiments. Features of various embodiments may be combined in other embodiments.

For purposes of explanation, specific configurations and details are set forth in order to provide a thorough understanding of the present subject matter. However, it will be apparent to one of ordinary skill in the art that embodiments of the subject matter described may be practiced without the specific details presented herein, or in various combinations, as described herein. Furthermore, well-known features may be omitted or simplified in order not to obscure the described embodiments. Various examples may be given throughout this description. These are merely descriptions of specific embodiments. The scope or meaning of the claims is not limited to the examples given.

Today, sleep monitoring is becoming available through various wearables, smart phone sleep applications, electroencephalogram (EEG) headsets, or even mats installed on top/below mattresses. These types of solutions may analyze sleep duration, interruption and even quality of sleep in some cases. Embodiments described herein also collect data from the environment to characterize possible triggers for sleep interruption, and analyze the sleep environment (e.g., sound events, sound levels, temperature, light, humidity, etc.). Sleep data is correlated with environmental data over an extended period of time to capture systemic issues with sleep interruptions/quality for the different environmental factors. This correlation may provide users with concrete evidence of what is impacting their sleep. Based on the results of the analysis, the system may suggest a change in the environment, if there is no variability in the data collected. For example, if the bedroom is in a noisy environment and all the data collected show constant noise, then it is hard to assess the advantage of a less noisy environment, other than by conjecture. The system may recommend that the user perform A/B testing on the factors that are not varying in the dataset. A/B testing, sometimes called split testing, is a term for a randomized experiment with two variants, A and B, which are the control and variation in the controlled experiment. In other words, in this context, a user will first try sleep with environmental factor A and then try sleep with environmental factor B. The results of factors A and B are compared to determine which factor improves sleep quality. The user may try each factor temporarily, and when the system has enough data to determine which factor provides a better solution, implement the better solution.

Figure 1:
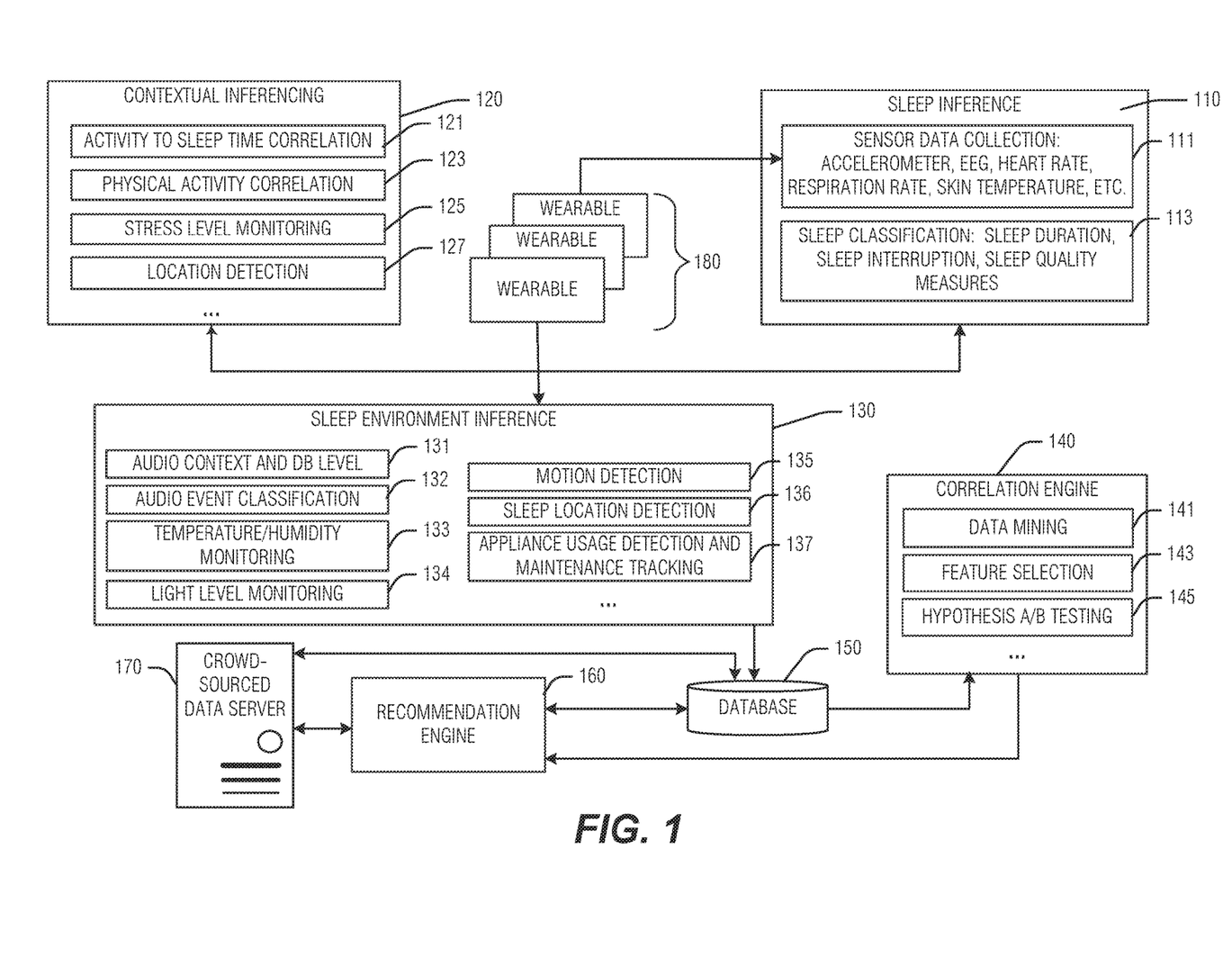
FIG. 1 is a block diagram illustrating components of a sleep and environment monitor and recommendation engine, according to an embodiment.

FIG. 1 is a block diagram illustrating components of a sleep and environment monitor and recommendation engine, according to an embodiment. Sleep inference logic 110 may include logic for sensor data collection 111 and sleep classification 113. Sleep inference logic 110 may analyzes sleep data provided by a number of sensors. For instance, sensor data collection 111 may include, but is not limited to, data collected by: an accelerometer on the person or sleep area (e.g., bed); heart rate monitor; EEG monitor; respiration monitor; skin temperature device; etc. The sleep inference logic 110 may also include sleep classification logic 113 which infers sleep quality based on factors including: sleep duration; sleep interruption; etc. Sleep interruption and duration may be inferred by movement of the sleeper, heart or respiration differences, etc. For instance, if a sleeper gets up out of bed every 30 minutes, it may be inferred that the sleeper had frequent sleep interruptions. In another example, if the sleeper is only asleep for 4-5 hours, as measured by heart rate or respiration, then it may be inferred that the sleep duration was less than optimal. Various parameters may be preset for different users. For instance, one user may feel rested after seven hours of uninterrupted sleep and another may require nine hours of uninterrupted sleep to feel rested. Sensor data may be provided by various wearable devices 180, head mounted devices (e.g., for EEG), or other infrastructure based devices.

Sleep environment inference logic 130 may be a combination of several modules or logic units that may analyze different aspects of the sleep environment. Audio analysis may be performed by logic units audio contexts and decibel level 131 and audio event classification 132. For instance a sound pressure level (SPL) for the ambient sound, defined as long-lasting and low energy, and audio events, defined as short duration and high-energy may be collected and analyzed. Long lasting audio signals may include, for instance, ambient sounds such as noise from an HVAC component, static noise, music, or other long duration environmental noises. These long lasting audio signals may be classified by the audio context and dB level classification logic 131. Short duration audio events may include sounds such as a baby crying, partner snoring, human speech, dog barking, toilet flushing, door closing, a car horn, or other specific short-term duration events, and may be classified by the audio event classification logic 132. In an example, snoring from another person in bed or outside the room may be extracted and identified in audio event classification logic 132 by using audio from two microphones in the room and triangulating the snoring audio to determine the location of the snorer. Initially, the system may be shipped with a generic classification model that works well across training data from a broad population of users. Over time the system may adapt to the particular user's environment by occasionally prompting the user to label sounds classified with low confidence levels. New audio classes may be trained for the user if sufficient labeled data can be obtained.

Temperature and humidity monitoring for indoor, outdoor and delta between the two may be collected and analyzed by the temperature humidity monitoring logic 133. Light level monitoring logic 134 may collect and monitor details about lights levels, for example, in immediate proximity of the user, as well as ambient light, for instance coming in through the window where there are cracks in the blinds. Motion detection logic 135 may receive sensor input from wearables 180 worn by the user, or other sensors located in the sleep environment, for instance accelerometers attached in or to the bed, to identify movement of the user or objects in the environment. In an example, a motion detector may be present in the room that may identify movement of any person, pet or object in the room. Motion may identify that the user's partner is tossing and turning in the bed, or that pet is pacing in the room, or jumping on and off of the bed, etc. Various wearables 180 may be used to detect movement of the user. For instance, a wrist worn accelerometer as in a smart watch or a motion sensor using Doppler information may be able to separate targets based on distance. Thus the Doppler input may enable the motion detecting logic 135 to distinguish between the user's movement and other movement. A correlation of the sensor data from multiple people in the home may be performed. For instance, sleep data may show interruption at the same time as other household members sleep.

Sleep location detection logic 136 may use wireless location sensing techniques to identify where a person is in the household. A semi-supervised learning approach may be used in sleep location detection logic 136 to identify personal significant places for user. For instance, the logic may infer which room the user is in and further in the case of bunk beds, for example, barometric readings may be used to infer whether the user is on the top or the bottom bunk or possibly on the floor. In an example, location and activity sensors may be used to infer that when a user dozes off in the living room and then later moves to the bedroom, the sleep quality is negatively impacted. The recommendation engine 160, to be described more fully below, may recommend that the user goes to the bedroom earlier in the evening.

Appliance usage detection and maintenance tracking logic 137 may identify various electrical signatures of appliances in the home using the analysis of the audio context and decibel level logic 131. Some appliances in the home need regular maintenance to avoid audio events that might disturb one's sleep. For instance, when a smoke alarm battery is low or completely discharged, the smoke alarm may produce a high-pitched chirping sound until the battery is replaced. The user may store maintenance event reminders in a database to include reminders for preventive or repetitive maintenance items in the home, as a reminder to perform the maintenance before sleep interrupting audio signals are produced by the appliance. It will be understood that the sleep environment factors and contextual factors as described herein are meant to be examples, and are not fully inclusive of factors that may be collected and used to correlate the sleep data.

Contextual inferencing logic 120 may include several modules or logic to provide contextual information correlating sleep activities with the environment and user status (e.g., physical and emotional state). Sometimes other factors might be causing sleep disruption that are not related to the environment. It may be useful to separate these human factors from the environmental factors. For example, physical activity information, such as, time of exercise or intensity of exercise may impact sleep. Other activities may have a correlation to sleep time, such as eating before bed, or watching scary movies, etc. Activity to sleep time correlation logic 121 may be used to identify various activities of the user throughout the day, or other historical period that may affect sleep. Physical activity correlation logic 123 may be used to identify the user's exercise time, exercise duration, and exercise intensity and correlate with sleep. These factors may be determined from data collected by a wearable

180, such as a wrist worn device, a smart phone application used to measure exercise, and/or sensors on the actual gym equipment that are configured be able to provide data via an Internet of things (IoT) protocol to the user's network. Stress level monitoring logic 125 may be used throughout the day to determine by physiological sensing, such factors to include: heart rate (HR), heart rate variability (HRV), galvanic skin response (GSR), audio sensing (e.g., stress from voice analysis), textual analysis or speech analysis (e.g., sentiment analysis of speech in written text), visual or perceptual sensing (e.g., facial expression detection), etc. Other factors in the user's activity profile may be identified, such as, calendar item analysis revealing back to back meetings, or minimal free time during the day, etc. Location detection logic 127 may catalog the user's location throughout the day for correlation with specific activities and stress identification. Analysis of physiological and contextual factors may be correlated to identify the times, location and magnitude of stressors.

Other factors may be used in the correlation such as the user's diet, sugar, caffeine or alcohol intake, etc. In an example, the user's food and beverage intake may be self-cataloged (e.g., journaled), or identified through visual or motion means. Food and beverage intake may also be inferred based on time, location and duration. For instance, if the user enters a coffee shop at 8 AM, as indicated by location identification and clock, intake of caffeinated beverage may be inferred. If the user enters a bar at 5 PM, an inference may be made that alcoholic beverages are being consumed at happy hour. If the user enters a gym where the user has a membership, and stays for 60 minutes, an inference of exercise may be made. Confidence of activity or food/beverage intake may be increased by correlating location, time and movement or visual images. In an embodiment, the system may prompt the user at a new location to identify an activity. If the user answers with the same activity multiple times, the confidence level of the inference may be increased. In an embodiment, the system may prompt the user only the first time a new location is identified, or prompt the user a pre-selected number of times to identify an activity. In an embodiment, the system may prompt the user for confirmation of activity in a frequented location at a pre-selected periodicity.

Activities outside of the sleep environment may be collected by a wearable or other device carried with the user, for later upload (or immediate transmission via a network) to the sleep and environmental monitoring system. In an example, if drinking, a user may repeat a motion or bending the elbow and raising a hand toward the mouth. Identification of drink vs. eating may be made by correlating analysis of either audio (e.g., chewing vs. drinking noises) or video (e.g., visually identifying food vs. drink). In an example, the user may update a profile indicating correlation between favorite places and activities for more accurate inferences. For instance, the user may conduct a regular 30 minute express workout twice per week, and a full 60 minute cardio workout once a week. The user may enter a predetermined correlation between a 60 minute stay at the gym with the 30 minute express workout, and a 90 minute stay at the gym with the 60 minute workout. Thus, confidence levels for inference based on those locations and activities may be improved.

Contextual inferencing logic 120 may use the factors to provide a correlation between activity levels and sleep quality. Cause and effect for these factors may be inferred, such as, exercise immediately prior to going to bed may adversely affect the user sleep. Other activities such as watching television or a movie on DVD may cause inferences as to the user's state of mind. For instance, when the user is watching a horror film or scary movie, the user's heart rate may increase and other anxiety levels may be measured by a variety of wearable devices. Thus, a correlation may be made between watching a scary movie immediately prior to bedtime and poor sleep quality. However, if the user watches the scary movie several hours prior to bedtime, this activity may not adversely affect sleep quality. Data related to factors such as activity, activity level, duration, diet, physiological factors, and proximity to bedtime may be collected and stored in a historical database for later correlation analysis, and comparison with other combinations of factors and correlated sleep quality measures.

Other physiological measurements may be collected, classified and used in the correlation. For instance, wellness indicators may be used to infer that the user does not sleep well when experiencing a cold, flu or taking certain medications. Illness factors may be observed through visual or audio means, for instance, if the user coughs a lot a cold may be indicated. In another example, the user may keep a running log of health or illness factors, or emotional state. Those factors will be associated with a time and location and may then be used in correlation with sleep quality.

Additional environmental context may be used in the contextual inference. For instance, weather and weather changes may affect the user's sleep quality. In an example, the user's location is identified and local weather information is accessed. Weather conditions and weather changes may be recorded for correlation. In an example, the user may find that sleep quality is decreased when the barometric pressure is low. In another example, the user may find that a quick shift from sunny weather to damp and dreary weather may cause sadness, which in turn may be inferred to cause poor sleep quality. Also weather may impact sleep quality due to the sound of thunder, rain hitting the windows, or loud wind blowing, etc.

In an embodiment, database 150 may store collected sensor data, user profiles and preferences, historical sleep sensing data, and sets of correlation data. In an embodiment, the database 150 may store the data from the sleep sensing, sleep environment inference and contextual inference logic components, to be used in mining for correlations, and recommendations. The database may also hold potential home improvement items and their effect on noise. For instance, if the current HVAC unit is noisy, recommendations for future replacement may be stored. Some factors related to environmental characteristics may be prepopulated in the database, while other factors may be learned over time (as discussed below). Items in the database may be flat, hierarchical or relational. A characteristic may be associated with a keyword to be used by mining recommendation and correlation logic. For example, a specific brand of recommended window blinds may be associated with a light rating, and be stored with a keyword "natural light control," as well as, other characteristics such as pricing, dimensions and automation requirements.

In an embodiment, correlation engine 140 is responsible for mining data, for instance stored in database 150, by the collection and analysis logic components, as described above. The correlation engine 140 may generate features from the various inference components and identify correlations across this robust and longitudinal dataset. The correlation engine 140 may identify these correlations, and generate hypothesis for the user for further A/B testing, to improve sleep quality. The correlation engine 140 may determine which environmental factors are likely to impact sleep most, given different contextual factors that occurred outside of sleep.

In an embodiment, historical information related to correlation of environmental factors with sleep quality for many users may be either stored in the database 150 or accessed from a local or network crowd-sourced data server 170. The crowd-sourced data server 170 may share and query some common sleep correlation data from other users. For example, a determined correlation may be that a memory foam bed helps during recovery from back surgery. In another example, a user may want to know if a certain type of triple pane window will block noise from siren and traffic noises in the user's neighborhood. The user may query the crowd-sourced data server 170 to see if any such correlations have been made by another user's correlation engine, and sent to the server 170, for similar criteria. In another example, a user may want to know for a house built by a certain builder in 1965, how soon floor boards need to be replaced or nailed down to prevent squeaking in high traffic areas. The sensed data, replacement history and effect of the floor board replacement may have been collected and tagged for future retrieval from the server 170. This environmental data, and subsequent analysis and correlation is learned in a specific household, and then optionally shared with others via the crowd-sourced data server 170. In an embodiment, a user may select which types of data may be shared, and which are to be kept private, in a user profile stored in either the database 150 and/or the server 170. A user may also choose that the data is anonymous or attributable to the user, in the profile.

In an embodiment, recommendation engine 160 is responsible for analyzing potential changes in the environment or user state, and providing the user with recommendations. The recommendation engine 160 may rely on state of the art collaborative filtering. In an embodiment, a user's budget, stored and maintained in database 150, in a user profile, may be factored in with other constraints and correlations for recommending a change in the environment. In an embodiment, the recommendation engine 160 may identify changes in home value, aesthetics, or even a multi-step improvement plan before providing a recommendation. In an embodiment, the recommendation engine 160 may receive advertisement and guarantee information for merchants (e.g., retailers, wholesalers, big box warehouse clubs, suppliers, etc.). The merchants may provide information on sound proofing window parameters for use in a recommendation for new windows, for instance, when the correlation engine 140 indicates that loud outdoor noises are the cause of poor sleep quality. The recommendation engine 160 may identify the sound proofing qualities of various windows offered, the pre-determined budget of the user, and historical data regarding dB of nighttime outdoor noise to make a recommendation for a specific window product for purchase. In an embodiment, the merchant may provide massage services to a user who has been experiencing poor sleep due to stress, and indicated in the contextual inferencing logic 120 and identified by the correlation engine 140.

Figure 2:
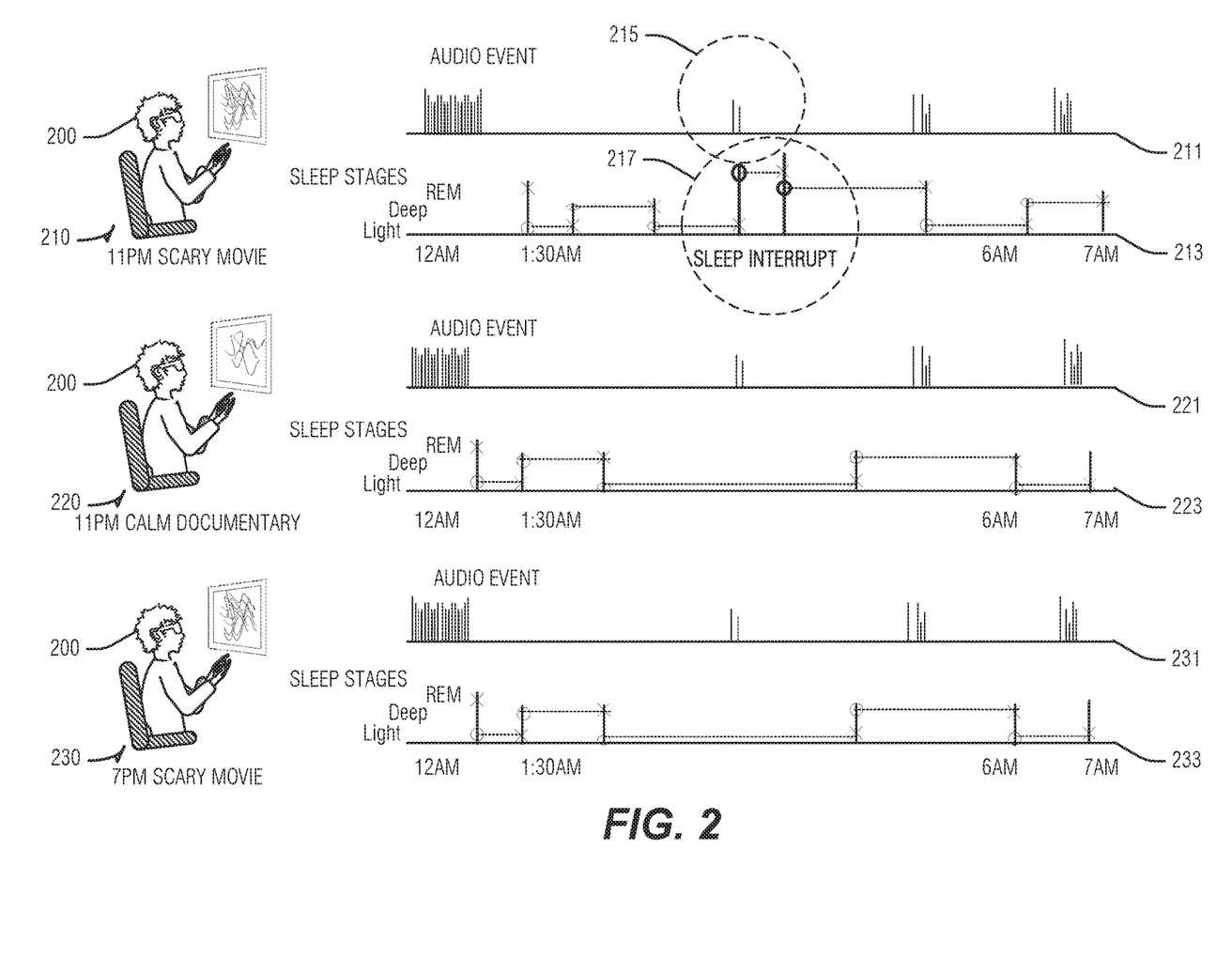
FIG. 2 is a diagram illustrating how a user's activities before bed may affect sleep quality, according to an embodiment.

FIG. 2 is a diagram illustrating how a user's activities before bed may affect sleep quality, according to an embodiment. In an example, watching television or a movie may be a classifiable event. In this example, three different scenarios are shown. The first scenario 210 illustrates user 200 watching a scary movie at 11 PM. The second scenario 220 illustrates user 200 watching a calm documentary at 11 PM. The third scenario 230 illustrates user 200 watching a scary movie at 7 PM. Horizontal lines 211, 221 and 231 illustrate audio events occurring on the user's timeline from about midnight to 7 AM. It should be noted that for this example, the same audio events occur at the same time in each scenario 210,220, 230. Horizontal lines 213, 223 and 233 illustrate timelines for sleep stages and reactions to the various environmental audio events on the audio event timelines (211, 221, 231), corresponding to the respective pre-bedtime activity in scenarios 210, 220 and 230. Sleep stages are illustrated as light, deep and REM and each sleep stage commences with a small circle or "o," and terminates with a small "x." In this example, it can be seen that user 200 experiences a sleep interruption 217 at the time of audio event 215. In an example, audio event 215 is a car backfiring outside the bedroom window. The correlated data shows that user 200 sleeps blissfully through this potentially startling audio event 215 when the pre-bedtime activity was either watching a calm documentary in scenario 220, or watching a scary movie early in the evening in scenario 230. Correlation engine 140 may mine the data related to audio events and sleep interruptions with pre-bedtime activities. Recommendation engine 160 may use the correlated data to suggest to user 200 to watch a scary movie earlier in the evening or watch something else. In an embodiment, the recommendation engine 160 may have access to real time viewing activity of the user 200, and make the recommendation to the user 200 if a scary movie (e.g., horror category) is tuned in on the user's set top box or Internet feed (e.g., entertainment streaming sites such as provided by NETFLIX® or HULU®).

In an embodiment, a night's sleep may be described by a vector of features or elements that may contribute to the quality of the sleep. For instance, a qualitative measure of sleep may be derived from a weighted combination of feature vectors describing the a night's sleep, where components of the vectors may include such factors as: "duration of time in deep sleep," "duration of time in light sleep", "duration of time in REM sleep," "sleep duration," "number of sleep interrupts," "duration of sleep interrupts," "offset of go to sleep time from median habitual go to sleep time," "offset of go to bed time from median habitual go to bed time," "time to go to sleep," "audio events associated with sleep interrupt," "light levels associated with sleep interrupt," etc. In an example, correlation in the sleep measure may be calculated using Eq. (1).

$$\text{similarity} = \cos(\theta) = \frac{A \cdot B}{\|A\|\|B\|} = \frac{\sum_{i=1}^{n} A_i B_i}{\sqrt{\sum_{i=1}^{n} A_i^2} \sqrt{\sum_{i=1}^{n} B_i^2}}, \quad \text{Eq. (1)}$$

where $A_i$ and $B_i$ are components of vectors A and B, respectively.

In the example in FIG. 2, using the cosine similarity, it can be seen that scenario 220 and scenario 230 (e.g., 11 PM documentary and the 7 PM scary movie) are more similar to each other than either scenario 220, 230 is to scenario 210 (e.g., 11 PM scary movie). Thus, if scenario 220 is measured as qualitative good sleep, then it may be inferred that scenario 230 also resulted in good sleep. However, if the sleep interruption causes the night's sleep to be measured as bad, fair, interrupted, or some other measure other than good, then it may be inferred that watching scary movies close to bedtime has a causal relationship with bad sleep.

Figure 3:
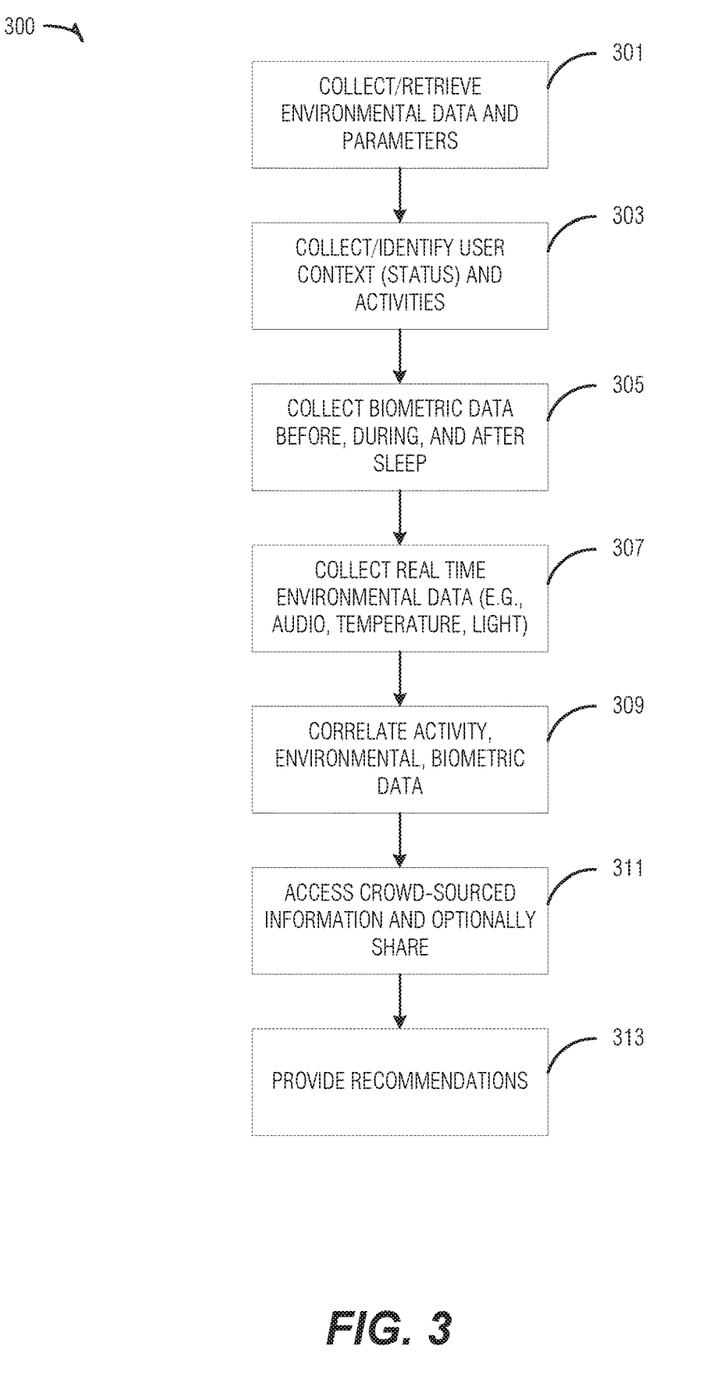
FIG. 3 is a flow diagram illustrating a method for monitoring sleep, environmental factors and other context for making recommendations, according to an embodiment.

FIG. 3 is a flow diagram illustrating a method 300 for monitoring sleep, environmental factors and other context for making recommendations, according to an embodiment. In an embodiment, a system for sleep and context monitoring may collect or retrieve environmental data and parameters in block 301. Information about the environmental context, for instance, lighting, noise, room dimensions and parameters, etc., may be retrieved from the database based on a determination of the user's location and time of day. An initial set of parameters for the environment may be preset in the database. User context may be collected and inferred in block 303. Various criteria for the user may be collected, such as, emotional state, physical state, recent activity, stress level, etc., as discussed above. This contextual data may be stored in a database, and/or be sent directly to a correlation engine.

Biometrics and other sleep data, herein referred to as sleep data for simplicity, may be collected in real time just prior to, during, and just after a sleep cycle of the user, in block 305. Sleep data may be collected from wearables, motion detectors, cameras, microphones, etc. to identify the state of the user before, during and after sleep. A set of data may be associated with a specific sleep cycle. A sleep cycle may include the time duration from beginning of sleep until the user gets up in the morning (or evening of on night shift, for instance). A sleep cycle may include a period immediately prior to sleep and immediately after waking up. The extension of time on either end may be pre-programmed or user definable. This data may be tagged with: a user ID (e.g., an anonymous identification or distinctive identification); location, time/date (e.g., temporal factor tag); and other information to be used for correlating with environmental factors. Environmental data may be collected in real time during a sleep cycle in block 307. Various environmental factors may be collected or inferred, as discussed above, such as, but not limited to, audio events, long duration audio, temperature, light, location in sleep area, orientation or position of the user relative to other environmental elements, etc. The biometric and sleep data, and environmental data may be stored in the database and/or send directly to correlation logic.

A module, logic or component for correlation may access or receive the contextual, environmental and sleep data to correlate various activities with user and environmental context, in block 309. A correlation may be associated with a sleep quality measurement for use in recommending improvements and/or to provide to a crowd-sourcing component. For instance, a pre-bedtime activity may be correlated with a stress level, time of day, location, environmental factors, and sleep quality index as components of the correlation. In example, as discussed above for scenario 210, a correlation may include the following factors: activity=scary movie within 30 minute sleep; stress level high, as indicated by blood pressure and heart rate; date/time=2017-Feb-01/ 00:00 PST; location=bedroom facing east; environment=dark95%, 10 dB long duration, 45 dB event at 03:30 PST; sleep quality=5 (out of 10). Sleep quality may be measured and inferred based on user feedback or objective measures such as wakefulness, or how long it takes to fall asleep again after an interruption, biometrics upon waking (e.g., bloodshot eyes, constant yawning, cheerfulness, etc.). Based on user preferences, multiple correlations may be formed from the same data, or subsets of data, for the same or similar time periods. In an example, pre-sleep activities may be omitted and just the stress level used in the correlation. Using various subsets enables an inference engine to infer a good or poor sleep quality based on a stress level, regardless of what caused the stress level. These subsets, or more generic or specific correlations may be helpful for future correlations, recommendations, or crowd-sourcing. If a user opts-in, correlations may be shared with a crowd-source data server, either locally or over a network such as the Internet, to a cloud server. A user may set a level for sharing in a local profile. For instance, the user may choose to mask, obscure or redact information including distinct identification, geographic location, pre-sleep activities, etc.

In an embodiment, a recommendation engine accesses correlations provided by other users from the crowd-source data server, in block 311. Correlations, with or without crowd-sourced data, may be stored and/or forwarded to the recommendation engine. The recommendation engine may access various levels of correlations and user profile data to provide the user with one or more recommendations, in block 313. In an example, only correlations that have similar criteria for a subset of factors may be deemed relevant and used for recommendation. For instance, a default relevance rule set may be provided with the sleep and context monitoring system. In an embodiment, the user may modify these parameters. For example, a user may only want to use crowd-sourced data from users with specific common demographics (e.g., age, ethnicity, weight, height, geographic area, etc.). The recommendation engine may retrieve information about user budget, static environment factors (e.g., window shade light blocking levels, ambient or long duration appliance noise, frequency of audio events above a dB threshold, geographic location, usual room temperature and humidity, etc.). The recommendation engine may include a number of rules or inference-based learning that identifies factors that are modifiable (e.g., replacing shades, windows, appliances, changing behavior or activities, obtaining a device to mitigate snoring or sleep apnea in the user or user's partner, etc.). Once potential changes are identified that are likely to improve the user's sleep quality, the recommendation(s) may be stored in the database for later retrieval or sent to the user via email, short message service, automated recorded telephone call, or other means. Once the user implements a recommended change, this change may be identified when environmental data and parameters are collected for a subsequent iteration of monitoring, inference, correlation and recommendation.

Figure 4:
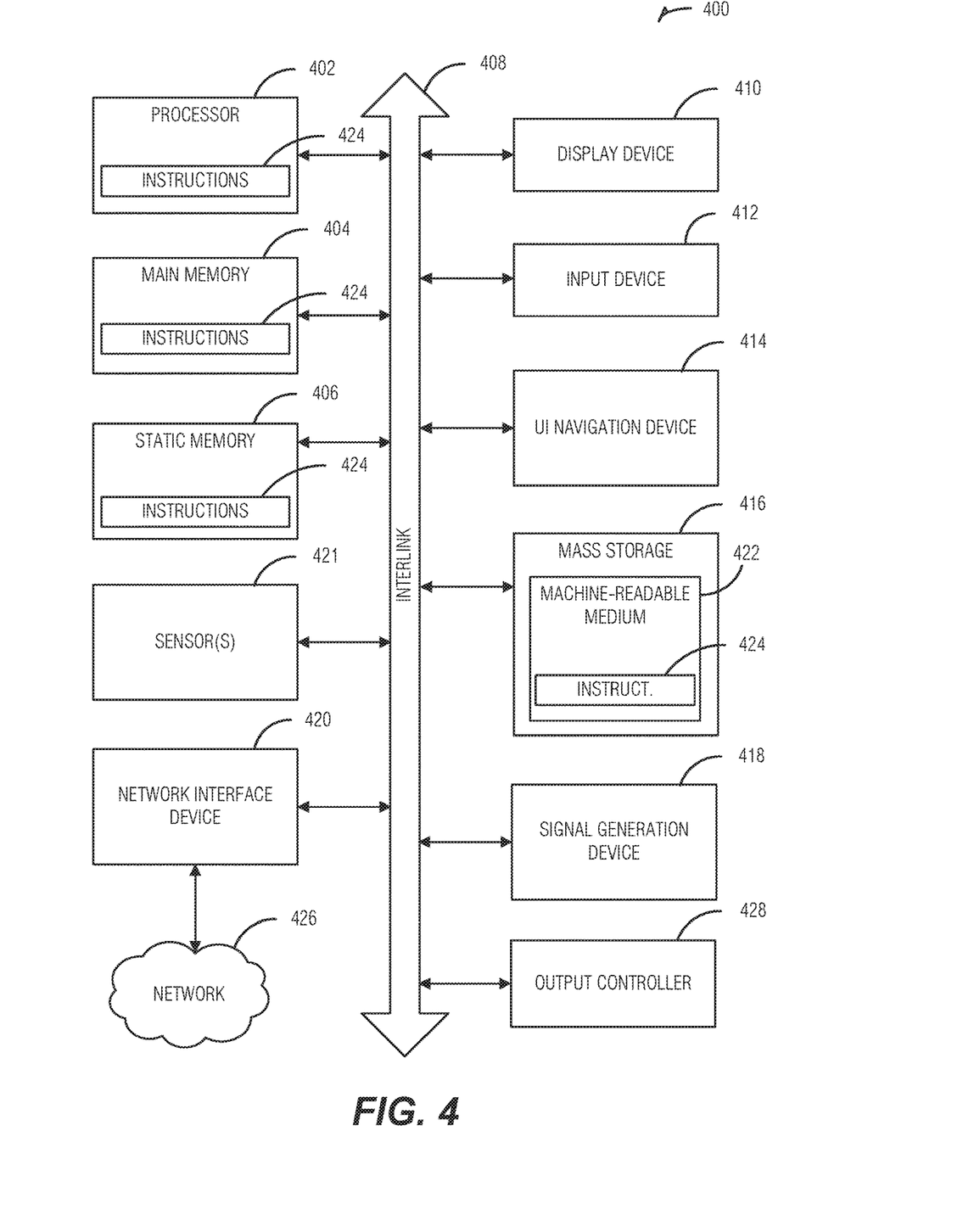
FIG. 4 is a block diagram illustrating an example of a machine upon which one or more embodiments may be implemented.

FIG. 4 illustrates a block diagram of an example machine 400 upon which any one or more of the techniques (e.g., methodologies) discussed herein may perform. In alternative embodiments, the machine 400 may operate as a standalone device or may be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuitry is a collection of circuits implemented in tangible entities that include hardware (e.g., simple circuits, gates, logic, etc.). Circuitry membership may be flexible over time and underlying hardware variability. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, the computer readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time.

Machine (e.g., computer system) 400 may include a hardware processor 402 (e.g., a central processing unit (CPU), a graphics processing unit (GPU), a hardware processor core, or any combination thereof), a main memory 404 and a static memory 406, some or all of which may communicate with each other via an interlink (e.g., bus) 408. The machine 400 may further include a display unit 410, an alphanumeric input device 412 (e.g., a keyboard), and a user interface (UI) navigation device 414 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or other sensor. The machine 400 may include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 416 may include a machine readable medium 422 on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) configured to store the one or more instructions 424.

The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices, magnetic disks, such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 400, and includes digital or analog communications signals or other intangible medium to facilitate communication of such software.

ADDITIONAL NOTES AND EXAMPLES

Examples may include subject matter such as a method, means for performing acts of the method, at least one machine-readable medium including instructions that, when performed by a machine cause the machine to performs acts of the method, or of an apparatus or system for monitoring context related to sleep quality and providing recommendations to the user, according to embodiments and examples described herein.

Example 1 is a system for monitoring context related to sleep quality in an environment, comprising: a database configured to store sensor data, user profiles, user preferences, sleep data, a plurality of correlation data, environmental factors, and context data; a correlation engine to correlate the environmental factors with the context and sleep data corresponding to a user, the environmental factors, context and sleep data to be retrieved from the database, the correlation engine arranged to provide a set of correlated data, wherein the plurality of environmental factors, context and sleep data are to be collected by one or more sensors communicatively coupled to the system, when in operation; and a recommendation engine arranged to analyze the set of correlated data and at least one possible change, wherein the possible change is a change to either the environment or user behavior, and wherein the recommendation engine is arranged to provide at least one recommendation for change, wherein the at least one recommendation is to be stored in the database.

In Example 2, the subject matter of Example 1 optionally includes the one or more sensors communicatively coupled to the system, wherein the one or more sensors comprise at least one physiological, biometrical or environmental sensing device.

In Example 3, the subject matter of Example 2 optionally includes wherein the one or more sensors communicatively coupled to the system are selected from a group of sensors consisting of an accelerometer, a heart rate monitor, an EEG monitor, a respiration monitor, a skin temperature monitor, a motion detector, an ambient temperature monitor, an audio capture device, a video capture device, a sound pressure device, a wireless location sensing device, a barometric pressure monitor, a global positioning sensor, and a compass.

In Example 4, the subject matter of any one or more of Examples 1-3 optionally include contextual inferencing logic to identify, by inference, a context classification associated with sensor or perceptual readings, the readings associated with the user or the environment or behavior of the user, wherein the context classification is to be used by the correlation engine and provided with the set of correlated data.

In Example 5, the subject matter of Example 4 optionally includes wherein the contextual classification comprises at least one contextual factor associated with the user, the at least one contextual factor including duration of time in deep sleep, duration of time in light sleep, duration of time in REM sleep, sleep duration, number of sleep interrupts, duration of sleep interrupts, offset of go to sleep time from median of habitual go to sleep time, offset of go to bed time from median of habitual go to bed time, time to go to sleep, audio events associated with sleep interrupt, or light levels associated with sleep interrupt.

In Example 6, the subject matter of any one or more of Examples 4-5 optionally include wherein the contextual classification comprises at least one contextual factor associated with the user, the at least one contextual factor including sleep time, recent activity, stress level, or location.

In Example 7, the subject matter of any one or more of Examples 4-6 optionally include sleep environment inferencing logic to analyze aspects of the environment affecting sleep quality, wherein to analyze aspects of the environment is to classify measurable data associated with at least one short term or long term event, wherein the event classification is to be used by the correlation engine and provided with the set of correlated data.

In Example 8, the subject matter of Example 7 optionally includes wherein the at least one short term or long term event is associated with a person in the environment other than the user.

In Example 9, the subject matter of any one or more of Examples 7-8 optionally include wherein the aspects of the environment affecting sleep quality are to be collected by at least one of a wearable device worn by the user or a sensor in proximity of the environment.

In Example 10, the subject matter of any one or more of Examples 7-9 optionally include wherein the aspects of the environment affecting sleep quality include at least one of audio context, decibel level, temperature, humidity, light level, motion detection, or sleep location.

In Example 11, the subject matter of any one or more of Examples 7-10 optionally include sleep inference logic to analyze sensor data associated with a sleep cycle of the user, the analysis to identify, by inference, a sleep quality measure, the sleep quality measure to be used by the correlation engine and provided with the set of correlated data.

In Example 12, the subject matter of Example 11 optionally includes wherein a short term or long term event is associated with a person in the environment other than the user, and wherein the sleep inference logic is to correlate the short term or long term event with the sleep quality measure.

In Example 13, the subject matter of any one or more of Examples 11-12 optionally include wherein the sensor data associated with a sleep cycle of the user are to be collected by at least one of a wearable device worn by the user or a sensor in proximity of the user.

In Example 14, the subject matter of any one or more of Examples 1-13 optionally include wherein at least a portion of the set of correlated data is provide to a crowd-sourced data server to be used in making recommendations to a second user, wherein the portion is selected based on a profile associated with user that defines data permissible to share with the second user.

In Example 15, the subject matter of any one or more of Examples 1-14 optionally include wherein the recommendation engine is to access correlated data from a second user via a crowd-sourced data server, the correlated data from a second user to be used in the analysis of possible changes to the environment or behavior of the user to assist in providing the recommendation for change.

Example 16 is a computer implemented method for correlating context related to sleep quality, comprising: correlating at least one of static environmental data, context of a user, or environmental event data with sleep data of the user, as correlated sleep data, wherein the correlation is associated with a common temporal factor; identifying in the correlated sleep data, combinations of contextual and environmental factors that affect the sleep quality of the user; and providing a change recommendation to the user, wherein the change recommendation is to recommend a change in at least one of the static environment or user behavior.

In Example 17, the subject matter of Example 16 optionally includes accessing correlated sleep, environmental and context data associated with a second user for use in providing the change recommendation to the user.

In Example 18, the subject matter of Example 17 optionally includes accessing the data associated with the second user from a crowd-sourced data server.

In Example 19, the subject matter of any one or more of Examples 16-18 optionally include providing at least a portion of the correlated sleep data to a crowd-sourced data server to be used in making recommendations for a second user, wherein the portion is selected based on a profile associated with user, the profile defining data permissible to share with the second user.

In Example 20, the subject matter of any one or more of Examples 16-19 optionally include identifying static environmental data and parameters; identifying user context including physical state, emotional state, recent activity, or stress level; identifying sleep data of the user during a sleep cycle; and identifying an environmental event that occur during the sleep cycle, wherein the environmental event includes audio, visual or motion events of short or long duration, wherein the identified static environmental data and parameters, user context, sleep data of the user, and the environmental event are correlated in the correlating to provide a set of correlated data.

Example 21 is at least one computer readable storage medium having instructions for correlating context related to sleep quality stored thereon, the instructions when executed on a machine cause the machine to: correlate at least one of static environmental data, context of a user, or environmental event data with sleep data of the user, as correlated sleep data, wherein the correlation is associated with a common temporal factor; identify in the correlated sleep data, combinations of contextual and environmental factors that affect the sleep quality of the user; and provide a change recommendation to the user, wherein the change recommendation is to recommend a change in at least one of the static environment or user behavior.

In Example 22, the subject matter of Example 21 optionally includes instructions to: access correlated sleep, environmental and context data associated with a second user for use in providing the change recommendation to the user.

In Example 23, the subject matter of Example 22 optionally includes instructions to access the data associated with the second user from a crowd-sourced data server.

In Example 24, the subject matter of any one or more of Examples 21-23 optionally include instructions to: provide at least a portion of the correlated sleep data to a crowd-sourced data server to be used in making recommendations for a second user, wherein the portion is selected based on a profile associated with user, the profile defining data permissible to share with the second user.

In Example 25, the subject matter of any one or more of Examples 21-24 optionally include instructions to: identify static environmental data and parameters; identify user context including physical state, emotional state, recent activity, or stress level; identify sleep data of the user during a sleep cycle; and identify an environmental event that occur during the sleep cycle, wherein the environmental event includes audio, visual or motion events of short or long duration, wherein the identified static environmental data and parameters, user context, sleep data of the user, and the environmental event are correlated in the correlating to provide a set of correlated data.

Example 26 is a system for correlating context related to sleep quality, comprising: means for correlating at least one of static environmental data, context of a user, or environmental event data with sleep data of the user, as correlated sleep data, wherein the correlation is associated with a common temporal factor; means for identifying in the correlated sleep data, combinations of contextual and environmental factors that affect the sleep quality of the user; and means for providing a change recommendation to the user, wherein the change recommendation is to recommend a change in at least one of the static environment or user behavior.

In Example 27, the subject matter of Example 26 optionally includes means for accessing correlated sleep, environmental and context data associated with a second user for use in providing the change recommendation to the user.

In Example 28, the subject matter of Example 27 optionally includes means for accessing the data associated with the second user from a crowd-sourced data server.

In Example 29, the subject matter of any one or more of Examples 26-28 optionally include means for providing at least a portion of the correlated sleep data to a crowd-sourced data server to be used in making recommendations for a second user, wherein the portion is selected based on a profile associated with user, the profile defining data permissible to share with the second user.

In Example 30, the subject matter of any one or more of Examples 26-29 optionally include means for identifying static environmental data and parameters; means for identifying user context including physical state, emotional state, recent activity, or stress level; means for identifying sleep data of the user during a sleep cycle; and means for identifying an environmental event that occur during the sleep cycle, wherein the environmental event includes audio, visual or motion events of short or long duration, wherein the identified static environmental data and parameters, user context, sleep data of the user, and the environmental event are correlated in the correlating to provide a set of correlated data.

Example 31 is at least one computer readable storage medium having instructions for correlating context related to sleep quality stored thereon, the instructions when executed on a machine cause the machine to perform the method of any of Examples 16-20.

Example 32 is a system for correlating context related to sleep quality stored thereon, comprising means to perform the method of any of Examples 16-20.

Example 33 is a system configured to perform operations of any one or more of Examples 1-30.

Example 34 is a method for performing operations of any one or more of Examples 1-30.

Example 35 is at least one machine readable medium including instructions that, when executed by a machine cause the machine to perform the operations of any one or more of Examples 1-30.

Example 36 is a system comprising means for performing the operations of any one or more of Examples 1-30.

The techniques described herein are not limited to any particular hardware or software configuration; they may find applicability in any computing, consumer electronics, or processing environment. The techniques may be implemented in hardware, software, firmware or a combination, resulting in logic or circuitry which supports execution or performance of embodiments described herein.

For simulations, program code may represent hardware using a hardware description language or another functional description language which essentially provides a model of how designed hardware is expected to perform. Program code may be assembly or machine language, or data that may be compiled and/or interpreted. Furthermore, it is common in the art to speak of software, in one form or another as taking an action or causing a result. Such expressions are merely a shorthand way of stating execution of program code by a processing system which causes a processor to perform an action or produce a result.

Each program may be implemented in a high level procedural, declarative, and/or object-oriented programming language to communicate with a processing system. However, programs may be implemented in assembly or machine language, if desired. In any case, the language may be compiled or interpreted.

Program instructions may be used to cause a general-purpose or special-purpose processing system that is programmed with the instructions to perform the operations described herein. Alternatively, the operations may be performed by specific hardware components that contain hard-wired logic for performing the operations, or by any combination of programmed computer components and custom hardware components. The methods described herein may be provided as a computer program product, also described as a computer or machine accessible or readable medium that may include one or more machine accessible storage media having stored thereon instructions that may be used to program a processing system or other electronic device to perform the methods.

Program code, or instructions, may be stored in, for example, volatile and/or non-volatile memory, such as storage devices and/or an associated machine readable or machine accessible medium including solid-state memory, hard-drives, floppy-disks, optical storage, tapes, flash memory, memory sticks, digital video disks, digital versatile discs (DVDs), etc., as well as more exotic mediums such as machine-accessible biological state preserving storage. A machine readable medium may include any mechanism for storing, transmitting, or receiving information in a form readable by a machine, and the medium may include a tangible medium through which electrical, optical, acoustical or other form of propagated signals or carrier wave encoding the program code may pass, such as antennas, optical fibers, communications interfaces, etc. Program code may be transmitted in the form of packets, serial data, parallel data, propagated signals, etc., and may be used in a compressed or encrypted format.

Program code may be implemented in programs executing on programmable machines such as mobile or stationary computers, personal digital assistants, smart phones, mobile Internet devices, set top boxes, cellular telephones and pagers, consumer electronics devices (including DVD players, personal video recorders, personal video players, satellite receivers, stereo receivers, cable TV receivers), and other electronic devices, each including a processor, volatile and/or non-volatile memory readable by the processor, at least one input device and/or one or more output devices. Program code may be applied to the data entered using the input device to perform the described embodiments and to generate output information. The output information may be applied to one or more output devices. One of ordinary skill in the art may appreciate that embodiments of the disclosed subject matter can be practiced with various computer system configurations, including multiprocessor or multiple-core processor systems, minicomputers, mainframe computers, as well as pervasive or miniature computers or processors that may be embedded into virtually any device. Embodiments of the disclosed subject matter can also be practiced in distributed computing environments, cloud environments, peer-to-peer or networked microservices, where tasks or portions thereof may be performed by remote processing devices that are linked through a communications network.

A processor subsystem may be used to execute the instruction on the machine-readable or machine accessible media. The processor subsystem may include one or more processors, each with one or more cores. Additionally, the processor subsystem may be disposed on one or more physical devices. The processor subsystem may include one or more specialized processors, such as a graphics processing unit (GPU), a digital signal processor (DSP), a field programmable gate array (FPGA), or a fixed function processor.

Although operations may be described as a sequential process, some of the operations may in fact be performed in parallel, concurrently, and/or in a distributed environment, and with program code stored locally and/or remotely for access by single or multi-processor machines. In addition, in some embodiments the order of operations may be rearranged without departing from the spirit of the disclosed subject matter. Program code may be used by or in conjunction with embedded controllers.

Examples, as described herein, may include, or may operate on, circuitry, logic or a number of components, modules, or mechanisms. Modules may be hardware, software, or firmware communicatively coupled to one or more processors in order to carry out the operations described herein. It will be understood that the modules or logic may be implemented in a hardware component or device, software or firmware running on one or more processors, or a combination. The modules may be distinct and independent components integrated by sharing or passing data, or the modules may be subcomponents of a single module, or be split among several modules. The components may be processes running on, or implemented on, a single compute node or distributed among a plurality of compute nodes running in parallel, concurrently, sequentially or a combination, as described more fully in conjunction with the flow diagrams in the figures. As such, modules may be hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured, arranged or adapted by using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

While this subject matter has been described with reference to illustrative embodiments, this description is not intended to be construed in a limiting or restrictive sense. For example, the above-described examples (or one or more aspects thereof) may be used in combination with others. Other embodiments may be used, such as will be understood by one of ordinary skill in the art upon reviewing the disclosure herein. The Abstract is to allow the reader to quickly discover the nature of the technical disclosure. However, the Abstract is submitted with the understanding that it will not be used to interpret or limit the scope or meaning of the claims.

What is claimed is:

1. A system for monitoring context related to sleep quality in an environment, comprising:
   a database configured to store sensor data, user profiles, user preferences, sleep data, a set of correlated data, environmental factors, and context data, wherein the context data comprises one or more of a daily activity level of the user, a time between the user watching television and going to sleep, a location where the user falls asleep, a sound level in a sleep environment of the user, a light level in the sleep environment of the user, an alcohol consumption level of the user, or a caffeine consumption of the user, and wherein the sleep data comprises one or more of an amount of time the user slept, a heart rate of the user during sleep, a respiration of the user during sleep, how often sleep of the user is interrupted, or a quality of sleep of the user;
   processing circuitry;
   a correlation engine, implemented by the processing circuitry, to create the set of correlated data from the environmental factors, the context data, and the sleep data stored in the database to correlate the environmental factors with the context data and the sleep data corresponding to the user, wherein the environmental factors, the context data, and the sleep data are to be collected by one or more sensors communicatively coupled to the system, when in operation; and
   a recommendation engine, implemented by the processing circuitry, to analyze the set of correlated data, wherein the recommendation engine is arranged to:
      select, based on the set of correlated data, a combination of an environmental factor and a user behavior from the database;
      indicate to the user to perform a split test on the combination;
      monitor the user to detect a result of the split test based on a change in the sleep data collected while the split test is performed by the user; and
      provide, based on the result of the split test, a change to the environment or the user behavior, and wherein the at least one change is to be stored in the database.

2. The system as recited in claim 1, further comprising the one or more sensors communicatively coupled to the system, wherein the one or more sensors comprise at least one physiological, biometrical or environmental sensing device.

3. The system as recited in claim 2, wherein the one or more sensors communicatively coupled to the system are selected from a group of sensors consisting of an accelerometer, a heart rate monitor, an EEG monitor, a respiration monitor, a skin temperature monitor, a motion detector, an ambient temperature monitor, an audio capture device, a video capture device, a sound pressure device, a wireless location sensing device, a barometric pressure monitor, a global positioning sensor, and a compass.

4. The system as recited in claim 1, further comprising:
   a contextual inferencing engine implemented by the processing circuitry to identify, by inference, a context classification associated with sensor or perceptual readings, the readings associated with the user or the environment or behavior of the user, wherein the context classification is to be used by the correlation engine and provided with the set of correlated data.

5. The system as recited in claim 4, wherein the contextual classification comprises at least one contextual factor associated with the user, the at least one contextual factor including duration of time in deep sleep, duration of time in light sleep, duration of time in REM sleep, sleep duration, number of sleep interrupts, duration of sleep interrupts, offset of go to sleep time from median of habitual go to sleep time, offset of go to bed time from median of habitual go to bed time, time to go to sleep, audio events associated with sleep interrupt, or light levels associated with sleep interrupt.

6. The system as recited in claim 4, wherein the contextual classification comprise at least one contextual factor associated with the user, the at least one contextual factor including sleep time, recent activity, stress level, or location.

7. The system as recited in claim 4, further comprising:
   a sleep environment inferencing engine implemented by the processing circuitry to analyze aspects of the environment affecting sleep quality, wherein to analyze aspects of the environment is to classify measurable data associated with at least one short term or long term event, wherein the event classification is to be used by the correlation engine and provided with the set of correlated data.

8. The system as recited in claim 7, wherein the at least one short term or long term event is associated with a person in the environment other than the user.

9. The system as recited in claim 7 wherein the aspects of the environment affecting sleep quality are to be collected by at least one of a wearable device worn by the user or a sensor in proximity of the environment.

10. The system as recited in claim 7, wherein the aspects of the environment affecting sleep quality include at least one of audio context, decibel level, temperature, humidity, light level, motion detection, or sleep location.

11. The system as recited in claim 7, further comprising:
   a sleep inference engine implemented by the processing circuitry to analyze sensor data associated with a sleep cycle of the user, the analysis to identify, by inference, a sleep quality measure, the sleep quality measure to be used by the correlation engine and provided with the set of correlated data.

12. The system as recited in claim 11, wherein a short term or long term event is associated with a person in the environment other than the user, and wherein the sleep inference engine is to correlate the short term or long term event with the sleep quality measure.

13. The system as recited in claim 11 wherein the sensor data associated with a sleep cycle of the user are to be collected by at least one of a wearable device worn by the user or a sensor in proximity of the user.

14. The system as recited in claim 1, wherein at least a portion of the set of correlated data is provide to a crowd-sourced data server to be used in making recommendations to a second user, wherein the portion is selected based on a profile associated with user that defines data permissible to share with the second user.

15. The system as recited in claim 1, wherein the recommendation engine is to access correlated data from a second user via a crowd-sourced data server, the correlated data from a second user to be used in the analysis of possible changes to the environment or behavior of the user to assist in providing the recommendation for change.

16. A computer implemented method for correlating context related to sleep quality, comprising:
 correlating at least one of static environmental data, context data, or environmental event data of a user with sleep data of the user, wherein the context data comprises one or more of a daily activity level of the user, a time between the user watching television and going to sleep, a location where the user falls asleep, a sound level in the a sleep environment of the user, a light level in a sleep environment of the user, an alcohol consumption level of the user, or a caffeine consumption of the user, and wherein sleep data comprises one or more of an amount of time the user remains asleep, a heart rate of the user during sleep, a respiration of the user during sleep, how often sleep of the user is interrupted, or a quality of sleep of the user, as correlated sleep data, wherein the correlation is associated with a common temporal factor;
 identifying in the correlated sleep data, combinations of contextual and environmental factors that affect the quality of sleep of the user;
 selecting, based on the identified combinations of contextual and environmental factors that affect the quality of sleep of the user, a combination of an environmental factor and a user behavior;
 indicating to the user to perform a split test on the combination;
 monitoring the user to detect a result of the split test based on a change in the sleep data collected while the split test is performed by the user; and
 providing, based on the result of the split test, a change to the user, wherein the change is a change in at least one of the static environment or the user behavior.

17. The method as recited in claim 16, further comprising:
 accessing correlated sleep, environmental and context data associated with a second user for use in providing the change recommendation to the user.

18. The method as recited in claim 17, further comprising:
 accessing the data associated with the second user from a crowd-sourced data server.

19. The method as recited in claim 16, further comprising:
 providing at least a portion of the correlated sleep data to a crowd-sourced data server to be used in making recommendations for a second user, wherein the portion is selected based on a profile associated with user, the profile defining data permissible to share with the second user.

20. The method as recited in claim 16, further comprising:
 identifying static environmental data and parameters;
 identifying user context including physical state, emotional state, recent activity, or stress level;
 identifying sleep data of the user during a sleep cycle; and
 identifying an environmental event that occur during the sleep cycle, wherein the environmental event includes audio, visual or motion events of short or long duration, wherein the identified static environmental data and parameters, user context, sleep data of the user, and the environmental event are correlated in the correlating to provide a set of correlated data.

21. At least one non-transitory computer readable storage medium having instructions for correlating context related to sleep quality stored thereon, the instructions when executed on a machine cause the machine to:
 correlate at least one of static environmental data, context data, or environmental event data of a user with sleep data of the user, wherein the context data comprises one or more of a daily activity level of the user, a time between the user watching television and going to sleep, a location where the user falls asleep, a sound level in the sleep environment of the user, a light level in the sleep environment of the user, an alcohol consumption level of the user, or a caffeine consumption level of the user, and wherein the sleep data comprises one or more of an amount of time the user remains asleep, a heart rate of the user during sleep, a respiration rate of the user during sleep, how often sleep of the user is interrupted, or a quality of sleep of the user, as correlated sleep data, wherein the correlation is associated with a common temporal factor;
 identify in the correlated sleep data, combinations of contextual and environmental factors that affect the quality of sleep of the user;
 select, based on the identified combinations of contextual and environmental factors that affect the quality of sleep of the user, a combination of an environmental factor and a user behavior;
 indicate to the user to perform a split test on the combination;
 monitor the user to detect a result of the split test, based on a change in the sleep data collected while the split test is performed by the user; and
 provide, based on the result of the split test a change to the user, wherein the change is a change in at least one of the static environment or the user behavior.

22. The at least one medium as recited in claim 21, further comprising instructions to access correlated sleep, environmental and context data associated with a second user for use in providing the change recommendation to the user.

23. The at least one medium as recited in claim 22, further comprising instructions to access the data associated with the second user from a crowd-sourced data server.

24. The at least one medium as recited in claim 21, further comprising instructions to provide at least a portion of the correlated sleep data to a crowd-sourced data server to be used in making recommendations for a second user, wherein the portion is selected based on a profile associated with user, the profile defining data permissible to share with the second user.

25. The at least one medium as recited in claim 21, further comprising instructions to:
 identify static environmental data and parameters;
 identify user context including physical state, emotional state, recent activity, or stress level;
 identify sleep data of the user during a sleep cycle; and
 identify an environmental event that occur during the sleep cycle, wherein the environmental event includes audio, visual or motion events of short or long duration, wherein the identified static environmental data and parameters, user context, sleep data of the user, and the environmental event are correlated in the correlating to provide a set of correlated data.

* * * * *